(12) United States Patent
Yoon

(10) Patent No.: US 9,925,038 B2
(45) Date of Patent: Mar. 27, 2018

(54) SYSTEM AND METHOD FOR DESIGNING WAVEFRONT-GUIDED OPHTHALMIC LENSES

(71) Applicant: Geunyoung Yoon, Pittsford, NY (US)

(72) Inventor: Geunyoung Yoon, Pittsford, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 432 days.

(21) Appl. No.: 14/335,805

(22) Filed: Jul. 18, 2014

(65) Prior Publication Data
US 2014/0362341 A1    Dec. 11, 2014

Related U.S. Application Data

(63) Continuation of application No. PCT/US2013/022507, filed on Jan. 22, 2013.

(60) Provisional application No. 61/588,956, filed on Jan. 20, 2012.

(51) Int. Cl.
| | |
|---|---|
| G02C 3/00 | (2006.01) |
| G02C 7/00 | (2006.01) |
| G02C 7/02 | (2006.01) |
| A61B 3/00 | (2006.01) |
| A61F 2/14 | (2006.01) |
| G02C 7/04 | (2006.01) |
| A61F 2/16 | (2006.01) |

(52) U.S. Cl.
CPC ............ *A61F 2/145* (2013.01); *A61B 3/0025* (2013.01); *A61F 2/1637* (2013.01); *G02C 7/027* (2013.01); *G02C 7/028* (2013.01); *G02C 7/047* (2013.01); *G02C 2202/22* (2013.01)

(58) Field of Classification Search
CPC ...... A61F 2/145; A61F 2/1637; A61B 3/0025; A61B 3/1015; G02C 7/027; G02C 7/028; G02C 7/047; G02C 2202/22
USPC .......................................... 351/159.7–79, 247
See application file for complete search history.

(56) References Cited

U.S. PATENT DOCUMENTS

| | | | |
|---|---|---|---|
| 6,499,843 B1 | 12/2002 | Cox et al. | |
| 2002/0040219 A1* | 4/2002 | Nakamura | A61B 3/107 606/5 |
| 2004/0008323 A1 | 1/2004 | Williams | |
| 2004/0057014 A1* | 3/2004 | Altmann | A61B 3/1015 351/246 |
| 2005/0275801 A1* | 12/2005 | Jones | G02C 7/028 351/159.74 |
| 2005/0286018 A1* | 12/2005 | Yamaguchi | A61B 3/14 351/205 |
| 2008/0143963 A1* | 6/2008 | Lindacher | G02C 7/028 351/246 |
| 2009/0161071 A1* | 6/2009 | Dreher | A61B 3/1015 351/246 |

(Continued)

FOREIGN PATENT DOCUMENTS

| | | |
|---|---|---|
| WO | WO-94-23327 A1 | 10/1994 |
| WO | WO-2004-099858 A1 | 11/2004 |
| WO | WO-2011-025846 A1 | 3/2011 |

*Primary Examiner* — Bumsuk Won
*Assistant Examiner* — Collin X Beatty
(74) *Attorney, Agent, or Firm* — Nathan S. Smith; Mark I. Bentley; McDermott Will & Emery LLP

(57) ABSTRACT

The design of a corrective lens combines the measured aberration with decentration and rotation of the lens to design customized optical surface profiles to reliably achieve vision correction.

34 Claims, 7 Drawing Sheets

(56) References Cited

U.S. PATENT DOCUMENTS

| | | | |
|---|---|---|---|
| 2009/0225273 A1* | 9/2009 | Clutterbuck | G02C 7/048 351/159.02 |
| 2010/0309428 A1* | 12/2010 | Altheimer | G02C 7/021 351/159.42 |
| 2011/0019148 A1* | 1/2011 | Portney | G02C 7/041 351/159.06 |
| 2011/0025979 A1* | 2/2011 | Chehab | G02C 7/021 351/212 |
| 2011/0149229 A1* | 6/2011 | Gerligand | G02C 7/048 351/159.1 |
| 2011/0149241 A1* | 6/2011 | Dai | A61F 9/00806 351/205 |
| 2011/0157545 A1* | 6/2011 | Applegate | G02C 7/027 351/159.02 |
| 2013/0077045 A1* | 3/2013 | Gerligand | G02C 7/048 351/159.74 |

* cited by examiner

FRONT SURFACE CUSTOMIZED

WITH CONVENTIONAL SOFT CONTACT LENS

WITH CUSTOMIZED SOFT CONTACT LENS

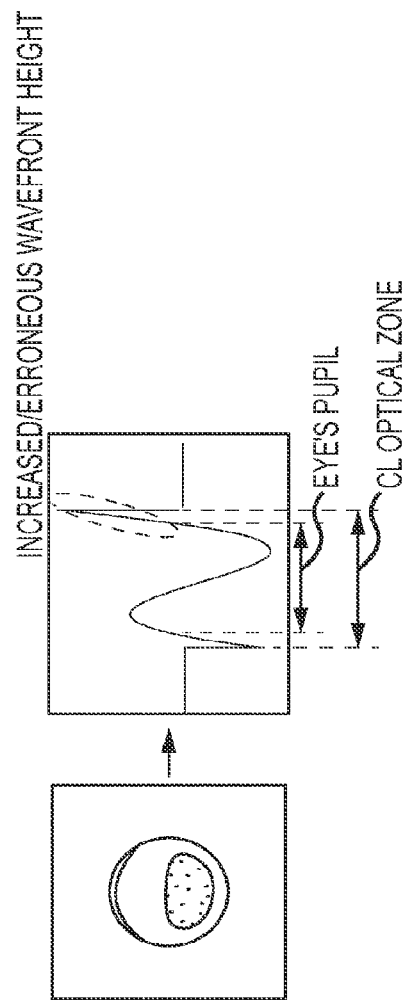
FIG. 4A EXTRAPOLATION
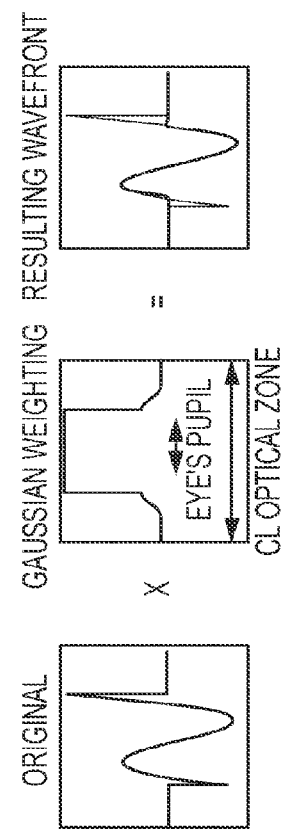
FIG. 4B GAUSSIAN WEIGHTING

EXTRAPOLATED ABERRATION

DECENTERED CONTACT LENS DESIGN

INCORPORATE MEASURED LENS DECENTRATION INTO WAVE ABERRATION

INCORPORATE MEASURED LENS ROTATION DURING MANUFACTURING

SYSTEM AND METHOD FOR DESIGNING WAVEFRONT-GUIDED OPHTHALMIC LENSES

REFERENCE TO RELATED APPLICATIONS

The present application is a continuation of International Patent Application No. PCT/US2013/022507, filed Jan. 22, 2013, entitled SYSTEM AND METHOD FOR DESIGNING WAVEFRONT-GUIDED OPHTHALMIC LENSES, which claims the benefit of U.S. Provisional Patent Application No. 61/588,956, filed Jan. 20, 2012, each of the foregoing applications being incorporated by reference in its entirety.

FIELD OF THE INVENTION

The present invention is directed to vision care and more particularly to higher-order aberration correcting/inducing ophthalmic lenses to improve visual performance.

DESCRIPTION OF RELATED ART

It has been well known that the human eye suffers from the optical defects called "wavefront aberrations," which include both lower (defocus and astigmatism) and higher order aberrations (those of higher order than defocus and astigmatism). Optical and psychophysical tests have demonstrated that correcting those aberrations significantly improves visual performance, especially when the pupil size is relatively large. The visual benefit is even more substantial when correcting the aberration in eyes with abnormal corneal conditions such as keratoconus and penetrating keratoplasty.

Adaptive optics is a powerful and noninvasive tool to achieve higher order correction. However, it is an impractical method. Although refractive surgery has been proven to be practical and effective to correct the aberration, it is a non-reversible surgical method, and its availability is restricted by factors such as corneal thickness and the amount of the aberration.

Vision correction using practical, noninvasive customized (or wavefront-guided) ophthalmic lenses to correct the aberration has been increasingly important. Those special optical components include phase plates (spectacles), soft and hard contact lenses, and intraocular lenses (IOLs). However, such vision correction still has its limits.

SUMMARY OF THE INVENTION

The invention is based on the inventor's realization that successful correction with those types of ophthalmic lenses requires (1) accurate measurement of the ocular aberration and (2) incorporating decentration and rotation of the lens with respect to the eye's pupil into the lens design. The measured aberration can include higher order aberration (that is, other than defocus and astigmatism, although they can include fifth- and higher order Zernike modes and even tenth-order Zernike modes). The invention implements a method for combining the measured aberration with decentration and rotation of the lens to design customized optical surface profiles to reliably achieve vision correction. Aspects of the invention are the method to measure the ocular aberration of the eye with the best fit conventional lens and to quantify the position and rotational orientation of the lens and techniques to effectively incorporate those measured values into the final two-dimensional lens surface profile.

BRIEF DESCRIPTION OF THE DRAWINGS

A preferred embodiment of the invention will be set forth in detail with reference to the drawings, in which:

FIGS. 4A-4D are diagrams showing the combination of lens movement and wavefront aberration when a lathing machine can fabricate only centered surfaces.

DETAILED DESCRIPTION OF THE PREFERRED EMBODIMENT

Figure 1A:
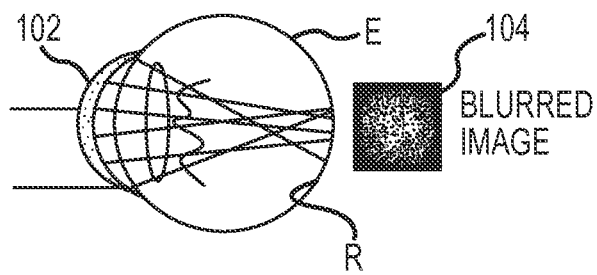
FIGS. 1A-1C are diagrams showing the concept of customized soft contact lenses.

A preferred embodiment of the present invention will be set forth in detail with reference to the drawings, in which like reference numerals refer to like elements or steps throughout.

Figure 1B:
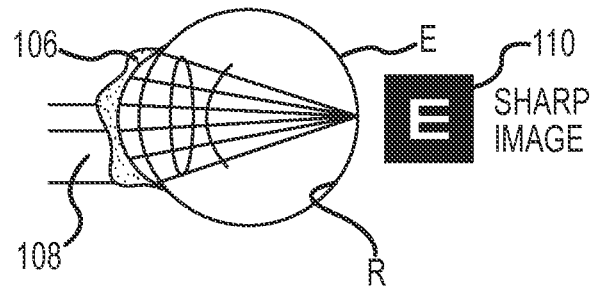
Figure 1C:
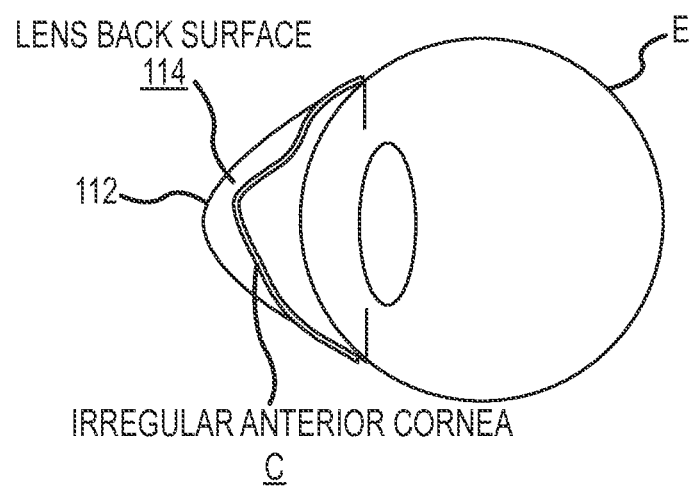

FIGS. 1A-1C illustrate the concept of customized ophthalmic lenses. As shown in FIG. 1A, a conventional lens 102 applied to the patient's eye E provides only a spectacle prescription, leaving the irregular higher-order aberrations uncorrected. That leads to a blurred image 104 on the retina R, especially for larger pupils and eyes with corneal abnormalities such as keratoconus and corneal transplants. As shown in FIG. 1B, a front-surface-customized ophthalmic lens 106 with an asymmetric surface profile 108 on the front side of the lens 106 corrects those higher-order aberrations to provide a sharp image 110.

In eyes with abnormal corneas, lens movements impair the correction performance, since the optical axis of the corrective lens is not aligned with the eye's optical axis. In order to reduce those lens movements, a back-surface-customized ophthalmic lens 112 can be implemented, as shown in FIG. 1C. Such lenses conform to the cornea C better, since they are designed with irregular back surface profiles 114 cut according to the patient's anterior cornea.

Figure 2:
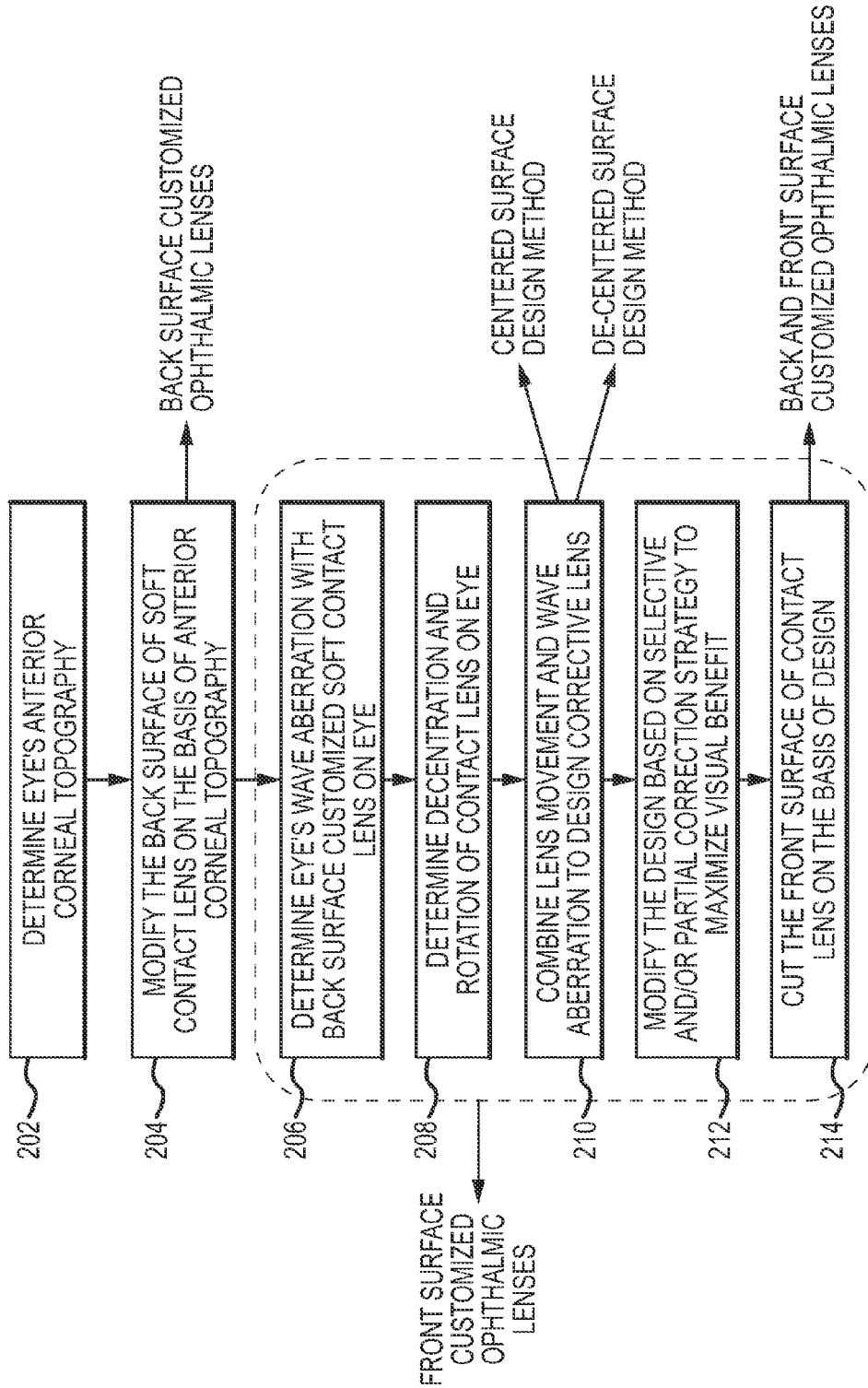
FIG. 2 is a flow chart showing the design of customized soft contact lenses according to the preferred embodiment.

FIG. 2 illustrates the step-wise procedure for designing customized ophthalmic lenses. First, in step 202, the anterior corneal topography of the subject is measured. The back surface of a conventional lens is cut according to those measurements in step 204, leading to the aforementioned back-surface-customized contact lens. That step is not necessary if the front-surface-only customization provides satisfactory outcomes and may also be eliminated for any practical issues such as time and cost. The front-surface-customized lens is designed next, either as an addition over the back surface lens or as a standalone correction. The eye's wave aberration is measured in step 206 either with a conventional lens or with the back surface lens. Techniques for measuring wave aberrations are known in the art and are disclosed, e.g., in U.S. Pat. No. 5,777,719. Images of the eye are also recorded simultaneously to aid in calculating the lens movements to determine the decentration and rotation of the contact lens in step 208. The corrective lens is designed by combining the lens movement and the wave aberration measurement in step 210 by one of two methods:

a centered or decentered surface design method. The designed profile can further be optimized by modifying the designed surface in step 212. Each higher-order aberration has a different impact on retinal image quality, and the higher the aberration order, the greater the sensitivity to the lens movements. Optimal selection of higher-order aberrations for which correction is attempted can be determined so that visual benefit can be maximized by minimizing the effects of the lens movements. From the measured movements of the lens over a period of time, a theoretical visual benefit can be evaluated by calculating improvement in image quality, e.g., the modulation transfer function with a different selection of aberrations to be corrected. The front surface of the lens is cut in step 214 according the final design obtained in the previous step.

Figure 3:
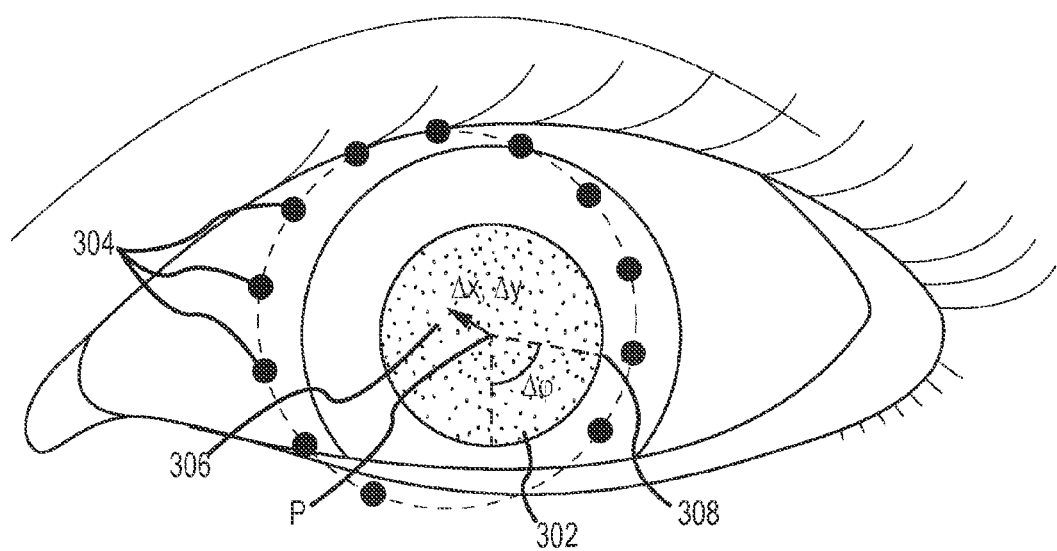
FIG. 3 is an annotated photograph showing the determination of lens decentration and rotation.

FIG. 3 shows the process of determining lens decentration and rotation. A conventional lens 302 with black marks 304 is worn by the subject. Using a camera and an existing automated computer algorithm, the center P of the pupil is estimated. Next, the center 306 of the lens 302 is estimated by calculating the center of the circle formed by joining the black marks. The vector displacement between the lens and pupil centers gives the horizontal ($\Delta x$) and vertical ($\Delta y$) decentration. Polar coordinates could be used instead. Rotation ($\Delta \varphi$) is obtained by calculating the orientation of a reference feature 308 from the vertical meridian (or any other previously determined default orientation).

Figure 4C:
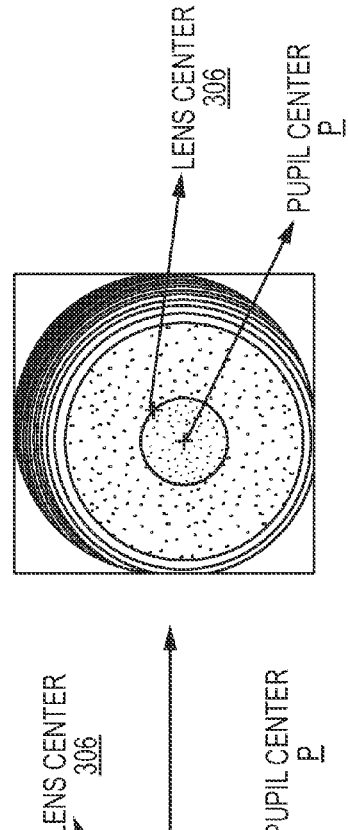
Figure 4C:
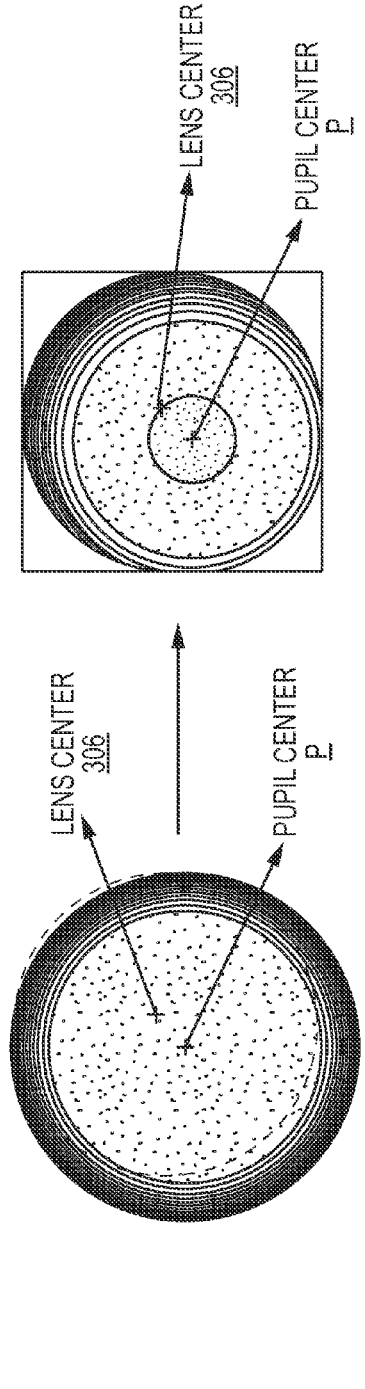

FIGS. 4A-4D show the process of lens design when the manufacturing process allows fabricating only centered optical surfaces. Rotational orientation is taken into account separately. The measured wave aberration of the eye is first extrapolated, as shown in FIG. 4A, to encompass the lens movement. However, extrapolation gives rise to increased and erroneous wavefront height at the edges of the optical zone. That leads to abrupt transition at the edge of the optical zone and increased lens material removal, thus leading to manufacturing errors.

Figure 4D:
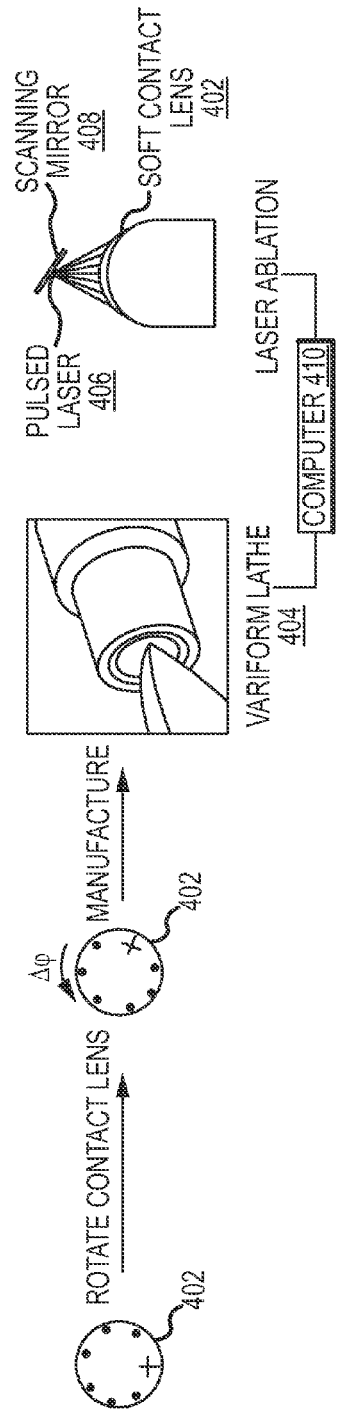

To overcome that problem, as shown in FIG. 4B, the extrapolated wavefront is then weighted with a function to smooth the transition between the optical zone and lens edge. That function is described by a flat top with unity amplitude in the center across the eye's pupil with a Gaussian or exponential decay at the edges. That same smoothing function will also be used in the decentered surface design method described below. The resultant wavefront overcomes the previously mentioned limitation related to extrapolation. That wavefront is then remapped around the center of the lens by accounting for the lens decentration, as shown in FIG. 4C. It is then fit to Zernike polynomials and serves as the final design of the ophthalmic lens in addition to its rotational orientation. During manufacturing, as shown in FIG. 4D, the ophthalmic lens is rotated optimally to account for the static rotation of the lens on the eye. That design algorithm provides a benefit that rotational orientation becomes an independent design parameter, unlike the decentered surface design method. The lens can be manufactured in any suitable manner. Two examples are the use of a variform lathe 404 and laser ablation using a pulsed laser 406 and a scanning mirror 408. The manufacturing process can be performed under control of a computer 410 that has been programmed to perform the operations disclosed in the present disclosure.

Figure 5:
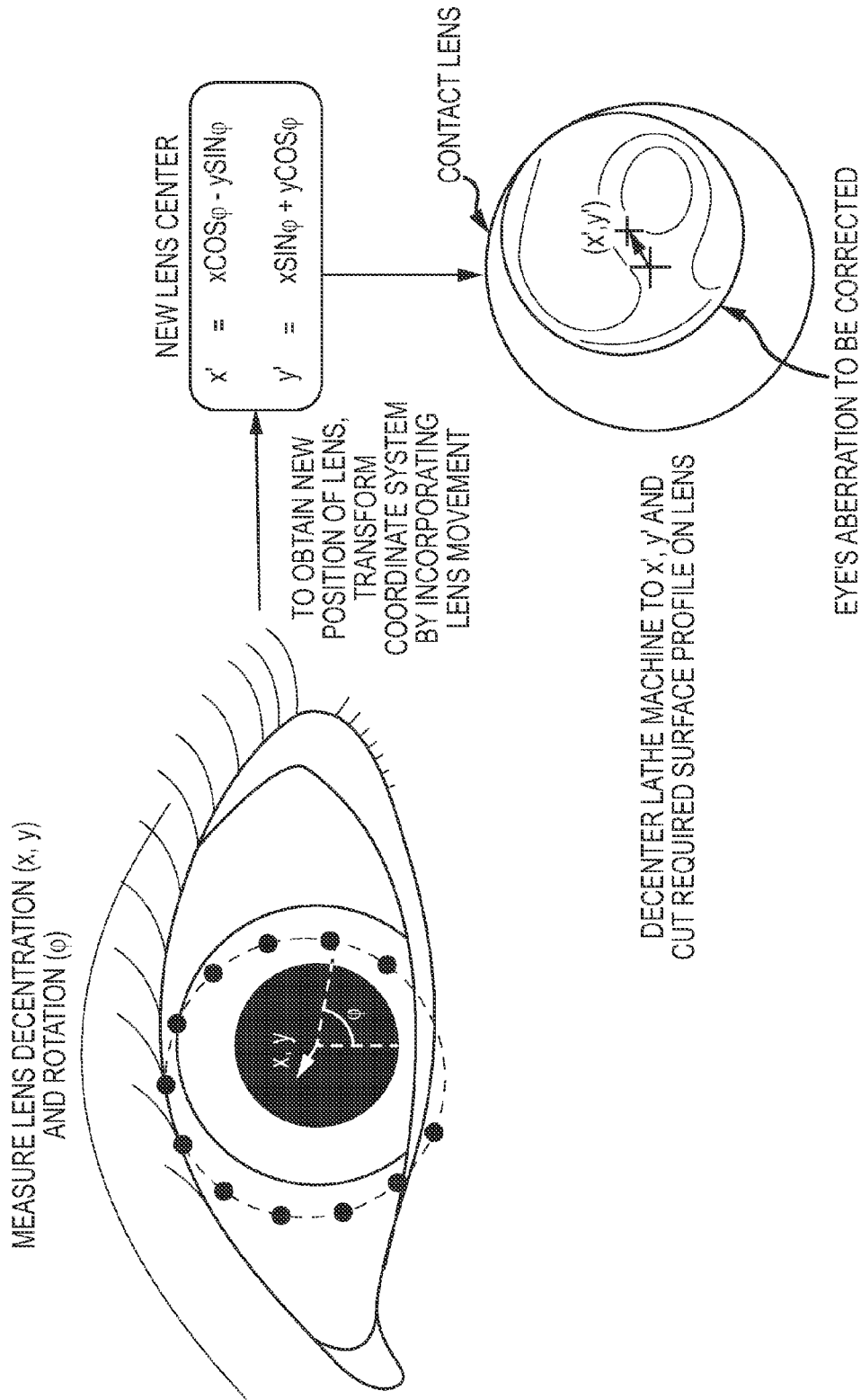
FIG. 5 is an annotated photograph showing the combination of lens movement and wavefront aberration when a lathing machine can fabricate decentered surfaces.

FIG. 5 shows the process of lens design when the manufacturing process allows fabricating decentered optical surfaces. Horizontal ($\Delta x$) and vertical ($\Delta y$) lens decentration and lens rotation ($\Delta \varphi$) are estimated in the same manner as described above. Rotational orientation is taken into account separately and is also part of coordinate transformation. A coordinate transformation to incorporate lens decentration in the presence of rotation is performed to find the new lens center (x', y'). The manufacturing process then modifies the surface profile of the lens with the new lens center as reference. During manufacturing, the lens is similarly rotated optimally to account for the static rotation. That method is a more direct and perhaps more reliable way of designing a customized surface, as it does not require the extrapolation process described above.

Variations of the preferred embodiment can include:
Back surface customization on the basis of corneal irregularity to stabilize lens movement;
Customized ophthalmic lenses by combining front and back surface customization;
Simultaneous recording of pupil images and eye's wave aberration to account for the effect of lens movement on optical correction;
Measurement of lens decentration and rotation;
  a. Lens marks to find lens center and pupil edge detection to find pupil center;
  b. Estimation of decentration by calculating vector displacement between pupil and lens center;
  c. Estimation of rotation by calculating orientation of a reference feature;
Combining lens movement and eye's wave aberration;
  a. Extrapolation and a weighting function to encompass lens decentration;
  b. Remapping of the wavefront around the center of the lens to account for lens decentration;
  c. Rotation of the ophthalmic lens before manufacturing to account for static rotation on eye;
  d. Transforming the coordinate system to account for the lens decentration in the presence of lens rotation;
Optimizing outcome benefits on the basis of the measured lens movement statistics; and
Any suitable combination of the above.

While a preferred embodiment of the present invention has been disclosed above, those skilled in the art who have reviewed the present disclosure will readily appreciate that other embodiments can be realized within the scope of the invention. For example, the data collection, computation, and fabrication can take place at the same location or remote locations. Therefore, the invention should be construed as limited only by the appended claims.

What is claimed is:

1. A method for producing an ophthalmic lens to correct vision in a patient's eye, the method comprising:

(a) receiving data taken from the eye into a computing device;

(b) automatically determining a wavefront aberration of the eye, the determining comprising:
extrapolating a wavefront having heights across an optical zone of the ophthalmic lens and a pupil of the eye; and
weighting the wavefront to smooth a transition of the wavefront between an edge of the pupil and the edge of the ophthalmic lens;

(c) automatically determining a rotation and decentration required for the ophthalmic lens relative to the pupil, wherein determining decentration comprises taking at least some of the data using a contact lens with a plurality of distributed lens marks on the patient's eye and calculating a center of a circle formed by the plurality of distributed lens marks; and (d) designing the ophthalmic lens in accordance with results of steps (b) and (c).

2. The method of claim 1, wherein step (b) comprises determining a higher-order aberration.

3. The method of claim 1, wherein step (d) comprises designing the ophthalmic lens with an irregular back surface profile according to determined anterior corneal topography of the patient's eye to stabilize movement of the ophthalmic lens.

4. The method of claim 1, wherein step (d) comprises designing front and back surfaces of the ophthalmic lens.

5. The method of claim 1, wherein the data received in step (a) comprise data from simultaneous recording of pupil images and the eye's wave aberration to account for the effect of lens movement on optical correction.

6. The method of claim 1, wherein:
step (c) comprises using pupil edge detection to find a pupil center.

7. The method of claim 6, wherein the decentration is estimated by calculating a vector displacement between the pupil center and a center of the contact lens.

8. The method of claim 1, wherein the rotation is estimated by calculating an orientation of a reference feature on the contact lens with the lens marks.

9. The method of claim 1, wherein step (d) comprises combining a lens movement and the eye's wave aberration.

10. The method of claim 9, wherein step (d) comprises using extrapolation and a weighting function to encompass the decentration.

11. The method of claim 9, wherein step (d) comprises remapping the wavefront around the center of the ophthalmic lens to account for the decentration.

12. The method of claim 9, wherein the ophthalmic lens is rotated before manufacturing to account for static rotation on the eye.

13. The method of claim 9, wherein a coordinate system is transformed to account for the lens decentration in the presence of lens rotation.

14. A system for producing an ophthalmic lens to correct vision in a patient's eye, the system comprising:
an input for providing data taken from the eye;
an output for outputting a lens design for fabrication; and
a computing device configured for:
  (a) receiving the data taken from the eye;
  (b) determining a wavefront aberration of the eye, the determining comprising:
    extrapolating a wavefront having heights across an optical zone of the ophthalmic lens and a pupil of the eye; and
    weighting the wavefront to smooth a transition of the wavefront between an edge of the pupil and the edge of the ophthalmic lens;
  (c) determining a rotation and decentration required for the ophthalmic lens relative to the pupil, wherein determining decentration comprises taking at least some of the data using a contact lens with a plurality of distributed lens marks on the patient's eye and calculating a center of a circle formed by the plurality of distributed lens marks; and
  (d) forming a lens design in accordance with results of steps (b) and (c).

15. The system of claim 14, wherein the computing device is configured to perform step (b) by determining a higher-order aberration.

16. The system of claim 14, wherein the computing device is configured to perform step (d) by designing the ophthalmic lens with an irregular back surface profile according to determined anterior corneal topography of the patient's eye to stabilize movement of the ophthalmic lens.

17. The system of claim 14, wherein the computing device is configured to perform step (d) by designing front and back surfaces of the ophthalmic lens.

18. The system of claim 14, wherein the computing device is configured such that the data received in step (a) comprise data from simultaneous recording of pupil images and the eye's wave aberration to account for the effect of lens movement on optical correction.

19. The system of claim 14, wherein the computing device is configured such that:
step (c) comprises using pupil edge detection to find a pupil center.

20. The system of claim 19, wherein the computing device is configured to estimate the decentration by calculating a vector displacement between the pupil center and a center of the contact lens.

21. The system of claim 14, wherein the computing device is configured to estimate the rotation by calculating an orientation of a reference feature on the contact lens with the lens marks.

22. The system of claim 14, wherein the computing device is configured to perform step (d) by combining a lens movement and the eye's wave aberration.

23. The system of claim 22, wherein the computing device is configured to perform step (d) by using extrapolation and a weighting function to encompass the decentration.

24. The system of claim 22, wherein the computing device is configured to perform step (d) by remapping the wavefront around a center of the ophthalmic lens to account for the decentration.

25. The system of claim 22, wherein the computing device is configured to control the output such that the ophthalmic lens is rotated before manufacturing to account for static rotation on the eye.

26. The system of claim 22, wherein the computing device is configured to transform a coordinate system to account for the lens decentration in the presence of lens rotation.

27. The system of claim 14, further comprising a camera in communication with the input.

28. The system of claim 14, further comprising a lens fabrication device in communication with the output.

29. The system of claim 28, wherein the lens fabrication device comprises a lathe.

30. The system of claim 28, wherein the lens fabrication device comprises a laser.

31. The system of claim 30, wherein the lens fabrication device further comprises a scanning mirror.

32. The method of claim 1, further comprising: (e) fabricating the ophthalmic lens in accordance with results of step (d).

33. The system of claim 14, wherein the computing device is further configured for: (e) outputting the lens design through the output.

34. A method for producing an ophthalmic lens to correct vision in a patient's eye, the method comprising:
(a) receiving data taken from the eye into a computing device;
(b) automatically determining a wavefront aberration of the eye, the determining comprising:
  extrapolating a wavefront having heights across an optical zone of the ophthalmic lens and a pupil of the eye; and
  weighting the wavefront to smooth a transition of the wavefront between an edge of the pupil and the edge of the ophthalmic lens;

(c) automatically determining a rotation and decentration required for the ophthalmic lens relative to the pupil; and
(d) designing the ophthalmic lens in accordance with results of steps (b) and (c).

\* \* \* \* \*